United States Patent
Oestreich

(10) Patent No.: US 8,849,397 B2
(45) Date of Patent: Sep. 30, 2014

(54) DEVICE FOR THE MEDICAL CARE OF A PATIENT IN AN EMERGENCY

(75) Inventor: Wolfgang Oestreich, Köln (DE)

(73) Assignee: Dr. Oestreich & Partner GmbH, Cologne (DE)

( * ) Notice: Subject to any disclaimer, the term of this patent is extended or adjusted under 35 U.S.C. 154(b) by 656 days.

(21) Appl. No.: 12/532,542

(22) PCT Filed: Mar. 20, 2008

(86) PCT No.: PCT/EP2008/053367
§ 371 (c)(1),
(2), (4) Date: Oct. 9, 2009

(87) PCT Pub. No.: WO2008/116822
PCT Pub. Date: Oct. 2, 2008

(65) Prior Publication Data
US 2010/0063556 A1    Mar. 11, 2010

(30) Foreign Application Priority Data
Mar. 23, 2007    (DE) .......................... 10 2007 014 136

(51) Int. Cl.
| | |
|---|---|
| A61N 1/00 | (2006.01) |
| A61B 5/08 | (2006.01) |
| A61B 5/0402 | (2006.01) |
| A61N 1/39 | (2006.01) |
| A61B 5/00 | (2006.01) |

(52) U.S. Cl.
CPC ................ *A61N 1/39* (2013.01); *A61B 5/0402* (2013.01); *A61B 5/6805* (2013.01); *A61B 5/0022* (2013.01); *A61N 1/3968* (2013.01); *A61B 5/417* (2013.01)
USPC .............................................. 607/3; 600/529

(58) Field of Classification Search
USPC ........................... 607/3, 5; 600/529, 388–389
See application file for complete search history.

(56) References Cited

U.S. PATENT DOCUMENTS

| | | | |
|---|---|---|---|
| 5,405,362 A | 4/1995 | Kramer et al. | |
| 5,833,711 A | 11/1998 | Schneider, Sr. | |

(Continued)

FOREIGN PATENT DOCUMENTS

| | | |
|---|---|---|
| DE | 69121470 | 8/1996 |
| EP | 459239 | 8/1996 |

(Continued)

OTHER PUBLICATIONS

International Search Report of the International Searching Authority for PCT/EP2008/053367 mailed Jan. 13, 2009 (5 pgs.).

*Primary Examiner* — Catherine Voorhees
(74) *Attorney, Agent, or Firm* — Harris Beach PLLC

(57) ABSTRACT

A device (1) for the medical care of a patient in an emergency which comprises an item of clothing (2) which may be worn by the patient on the body and monitoring devices (8, 9) arranged on the item of clothing (2), which may monitor at least one physiological function of the patient, in order to detect an emergency. The device further comprises a cardiac compression device (3, 4) arranged on the item of clothing (2), which is operatively connected to the monitoring device (8, 9), in order to treat the patient with a cardiac resuscitation when the monitoring device (3, 4) determines an emergency, and a defibrillator (5, 6, 7) as well as the intraosseous delivery of drugs into the bone marrow cavity of the breast bone. Moreover, a device (1) for the medical care of a patient in an emergency, which comprises as a therapeutic device a respiratory therapeutic device (10, 11, 12, 13) which is able to supply oxygen and/or a drug for pulmonary resuscitation into the respiratory system of the patient.

25 Claims, 2 Drawing Sheets

(56) References Cited

U.S. PATENT DOCUMENTS

| | | |
|---|---|---|
| 6,213,960 B1 | 4/2001 | Sherman et al. |
| 2004/0162587 A1 | 8/2004 | Hampton et al. |
| 2004/0215112 A1 | 10/2004 | Mollenauer et al. |
| 2004/0230140 A1 | 11/2004 | Steen |
| 2005/0126578 A1 | 6/2005 | Garrison et al. |
| 2007/0049945 A1* | 3/2007 | Miller .............................. 606/86 |
| 2007/0276278 A1* | 11/2007 | Coyle et al. ................... 600/529 |
| 2008/0114219 A1* | 5/2008 | Zhang et al. ................... 600/301 |
| 2008/0306560 A1* | 12/2008 | Macho et al. ..................... 607/5 |

FOREIGN PATENT DOCUMENTS

| | | |
|---|---|---|
| EP | 1550398 A1 | 7/2005 |
| WO | WO-9963926 | 12/1999 |

* cited by examiner

DEVICE FOR THE MEDICAL CARE OF A PATIENT IN AN EMERGENCY

This application is a national stage application under 35 U.S.C. §371 of PCT Application No. PCT/EP2008/053367 filed Mar. 20, 2008, which claims priority to and the benefit of German patent application Ser. No. 10 2007 014 136.1, filed Mar. 23, 2007, which is incorporated herein by reference in its entirety.

BACKGROUND TO THE INVENTION

The invention relates to a device for the medical care of a patient in an emergency.

Prior Art

A jacket which may be worn by a patient on the body is known from the European patent application EP 1 550 398 A1, which is provided with a plurality of sensors and therapeutic devices. A pressure sensor, a temperature sensor, a microphone and a biochemical sensor are provided, amongst others, as sensors. The sensors are intended to measure, amongst others, the blood pressure, the body temperature, the pulse, the oxygen level in the blood and the blood sugar level. An oxygen source, a pump, airbags, a hypodermic syringe and an electroshock device are provided, amongst others, as therapeutic devices. The airbags are intended, together with the pump, to correct the posture of the patient, to fix a broken bone in position, to stop bleeding or carry out cardiac resuscitation or a Heimlich maneuver.

The U.S. Pat. No. 5,544,661 discloses a patient monitoring system comprising a portable device and a base station. The portable device comprises, amongst others, an electrocardiograph and a photoplethysmograph. The system is able to analyse data detected thereby and, if necessary, notify a base station via a mobile telephone network, transmit physiological data of the patient thereto and create a voice communication. Moreover, therapeutic devices which are attached to the patient may be activated from the base station, for example an external defibrillator, a pace-maker or an automatic drug infusion device.

An external defibrillation and drug injection system is known from the U.S. Pat. No. 5,405,362, which is provided, in particular, for treating patients with cardiac disorders away from hospital. The system comprises a device which is able to monitor a plurality of physiological parameters of the patient, and an expert system which makes recommendations for treatment to an operator. Moreover, it comprises an external defibrillation device and a device for the automatic injection of a drug into the bone marrow shown in FIG. 3 herein), by means of which the operator is able to treat the patient.

The U.S. Pat. No. 5,156,148 discloses a system for the automatic treatment of cardiac malfunction without human intervention. The system receives physiological signals from the patient, which relate to the circulatory system thereof, and processes said signals using a microprocessor. The microprocessor controls treatment devices, including a defibrillator and a device for intravenous drug delivery.

Finally, a system for the mobile monitoring of the cardiac function of a patient is known from the German Utility Model DE 20 2005 02 525 U1. In the system, electrodes for forwarding an electrocardiogram are connected wirelessly, or by electrodes running in an item of clothing, to a central control unit. The central control unit is able to store and process the electrocardiogram data, as well as transmit a message to an external receiver and create a voice communication therewith. It further comprises a GPS unit for positioning the system. An interface on the central control unit allows the transmission of the data to an external medium.

The Problem Underlying the Invention

The object of the invention is to provide an improved device for the medical care of a patient in an emergency.

Solution According to the Invention

To solve the object, the invention teaches a device for the medical care of a patient in an emergency which comprises an item of clothing, wherein the item of clothing is worn by the patient on the body, a monitoring device arranged on the item of clothing that monitors at least one physiological function of the patient to determine an emergency, and a therapeutic device for treating the patient when the monitoring device determines an emergency, wherein the therapeutic device is arranged on the item of clothing, and operatively connected to the monitoring device, and wherein the therapeutic device is selected from the group consisting of a respiratory therapeutic device that endotracheally supplies oxygen, an oxygen-containing gas mixture and/or at least one drug wherein the respiratory therapeutic device comprises a puncture unit for perforating the trachea of the patient below the larynx and wherein the monitoring device can without the active involvement of the patient or a third party trigger the perforation when it determines an emergency, and a puncture device that delivers a drug in an intraosseous manner.

To solve the object, the invention further teaches a device for the medical care of a patient in an emergency with the features of claim 3. As the therapeutic device comprises a respiratory therapeutic device, in an emergency it may be achieved by means of the invention to obtain access to the respiratory system of the patient, in particular to carry out life-saving measures.

The invention may be used, in particular, for patients who are at an increased risk, due to an existing cardiac-circulatory disorders, of suffering a sudden cardiac arrest or cardiac movements which produce no cardiac output (for example palpitations) or respiratory arrest. The emergency may, in particular, be a cardiac arrest or respiratory arrest. It may be achieved by means of the invention to reduce the probability that a patient dies as a result of the emergency.

As the monitoring and therapeutic devices are arranged on the item of clothing, it is possible to provide a device which may be worn on the body. This may, in particular, contribute to the increase in the mobility of the patient and improve the quality of life thereof. It may be achieved by means of the invention that monitoring and treatment of the patient takes place without the active involvement thereof or that of a third party. As the monitoring device and the therapeutic devices are operatively connected, the monitoring device, when it determines an emergency, may trigger a treatment or different treatments in a logical medical sequence or simultaneously as a result of the therapeutic devices.

Structure and Development of the Solution According to the Invention

Advantageous embodiments and developments which may be used individually or in combination with one another form the subject-matter of the dependent claims.

The device according to the invention preferably comprises a defibrillator as a therapeutic device. Preferably, the defibrillator is arranged on the item of clothing. The preferred defibrillator may carry out cardioversion and/or defibrillation. It preferably comprises at least two electrodes, which may be attached to the patient preferably on the chest wall thereof, in order to supply the patient with a sufficient current impulse for defibrillation. The electrodes are preferably gel-releasing electrodes which, before the application of the current impulse, release a conductive gel between the electrode and the chest wall or allow protection of the skin in a different manner.

A preferred defibrillator is operatively connected to the monitoring unit. Preferably, the defibrillator carries out defibrillation or cardioversion, when the monitoring device detects a cardiac arrest, at certain time intervals and with increasing intensity, until the monitoring device detects a restoration of cardiac activity, or until the defibrillator is deactivated externally, for example by a paramedic from a rescue service.

Preferably, the device according to the invention comprises as a therapeutic device a cardiac compression device for cardiac resuscitation. With this embodiment of the invention it may be achieved that a minimal circulation is again produced and/or maintained in patients. Preferably, the monitoring device may trigger the cardiac compression, when it determines a cardiac arrest and may particularly preferably be carried out for a sufficient length of time until it detects the reinstatement of cardiac activity or until the cardiac compression device is deactivated externally, for example by a paramedic of a rescue service.

The cardiac compression device is preferably controlled such that a resting phase respectively follows a predetermined number of cardiac compressions, in which other therapeutic measures may be carried out, preferably by one or more different therapeutic devices of the device (for example artificial respiration, intraosseous drug delivery). The cardiac compression device is preferably controlled such that when the patient is also treated with the defibrillator, the cardiac compressions respectively take place between the individual defibrillations and/or cardioversions. The preferred frequency of the cardiac compressions is between 30 and 200, preferably between 50 and 120 compressions per minute. The dwell time in the maximum compressed position is preferably the same as the relaxed position, i.e. the pressure phase and the relaxed phase are of the same length. A preferred cardiac compression device uses airbags which preferably are inflated and emptied by a pump, for example as disclosed in EP 1 550 398 A1. The relevant contents of the aforementioned document are incorporated into the present disclosure, by reference.

Preferably, the cardiac compression device presses the breast bone in the transition region from its central to its lower third against the spinal column, preferably by 2 to 12 cm, particularly preferably by approximately 6 centimetres. The preferred compression frequency is approximately 50 to 70, particularly preferably approximately 60, compressions per minute. A preferred cardiac compression device is, to this end, provided with a pneumatic plunger or spring mechanism. The bearing surface of the plunger is preferably between 2 to 10, particularly preferably approximately 5 centimetres wide and 5 to 20, particularly preferably approximately 10 centimetres long. In order to allow sufficient pressure against the spinal column, the item of clothing adopts a rigid state in the back region, at least for the respective duration of the cardiac compression.

A further preferred cardiac compression device operates according to the thorax pump method. Preferably, it comprises a substantially tubular airbag, for example similar to an oversized blood pressure sleeve, which is placed around the thorax and is insufflated and desufflated by means of a pneumatic device. With this embodiment of the invention, a substantially uniform compression of the entire thorax and thus a genuine reduction of the cross section of the thorax and, in particular, also the volume of the thorax may be achieved. The preferred insufflation pressure is between 150 and 350, particularly preferably approximately 250 millimeter Hg. The preferred compression frequency is approximately 50 to 70, particularly preferably approximately 60, compressions per minute. It is an achievable advantage of this embodiment of the invention that by the compression of the thorax a compression of the lungs may also be carried out. This may also contribute to the fact that in addition to minimal circulation, minimal respiration is also maintained.

A preferred cardiac compression device operates according to the principle of interposed abdominal counterpulsation (IAC-CPR). In this case, during the relaxation of the thorax, the abdomen is compressed in the region of the navel, for example by means of a plunger or by means of a substantially tubular airbag, as described above in connection with the thorax pump method. The pressure of the abdominal compression is preferably between 50 and 150 millimeter Hg. Preferably, the compression takes place according to the principle of interposed abdominal counterpulsation (IAC-CPR) with intubated patients. Additionally, the device according to the invention preferably comprises a suitable respiratory therapeutic device, particularly preferably as disclosed below. In a preferred modification of the interposed abdominal counterpulsation, a continuous compression of the abdomen takes place, i.e. also exerted during the thorax compression, also denoted as "abdominal binding".

The cardiac compression device comprises, in a preferred embodiment, means in order to lift the thorax during the relaxed phase. Such a cardiac compression device may operate according to the method of active compression-decompression (ACD-CPR). In this embodiment of the invention it may be achieved that an intrathoracic vacuum is produced, in order to improve the diastolic venous return. This may increase both the intrathoracic blood volume and improve the ventilation of the lungs. Particularly preferably, the cardiac compression device combines the active compression-decompression with the interposed abdominal counterpulsation. To this end, it may for example comprise two plungers, respectively one thereof being able to be attached to the thorax and one to the abdomen, and which are preferably connected to one another via a lever. Then alternately, as with two weighing scale pans, either the thorax is compressed and the abdomen decompressed (systole) or vice versa.

In a preferred modification of the aforementioned method for cardiac compression a higher compression frequency is used, preferably between 100 and 200, particularly preferably between 120 and 150 compressions per minute. An achievable advantage of this embodiment of the invention is an increased heart-time-volume through flow.

A preferred device according to the invention comprises a puncture device which may deliver a drug in an intraosseous manner, particularly preferably into the bone marrow. The puncture device preferably comprises a cannula, in order to puncture a bone, particularly preferably the breast bone. With this embodiment of the invention it may be achieved to gain access to the bone marrow cavity, in order thereby, preferably through the cannula, to administer injectable or infusible drugs from a drug reservoir. A similar mechanism may, for example, be used as the autoinjection mechanism disclosed in U.S. Pat. No. 5,405,362 (see FIG. 3 herein). The relevant content of the aforementioned document are incorporated into the present disclosure by reference.

Instead of, or in addition to, the endotracheal access of the respiratory therapeutic device, the puncture device according to the invention may advantageously provide a similarly advantageous intraosseous administration route. The puncture device is preferably arranged on the item of clothing. It is preferably operatively connected to the monitoring device. In a preferred embodiment of the invention, the puncture device is integrated at least partially in a sub-assembly with the cardiac compression unit.

In a preferred embodiment, the invention comprises a respiratory therapeutic device which is able to supply oxygen and/or at least one drug endotracheally. The respiratory therapeutic device is preferably arranged on the item of clothing. It is preferably operatively connected to the monitoring device. A preferred respiratory therapeutic device comprises a puncture unit, in order to perforate the trachea below the larynx. The monitoring device may trigger the perforation when it determines an emergency.

A preferred puncture unit comprises a semi-circular puncture cannula, preferably with a diameter of between 5 and 20 millimeter, particularly preferably between 8 and 16 millimeter. It further preferably comprises a flap mechanism, particularly preferably a spring-loaded flap mechanism, in order to drive the puncture cannula towards the lungs into the trachea. A similar mechanism may, for example, be used as the auto-injection mechanism disclosed in U.S. Pat. No. 5,405,362.

Preferably, the respiratory therapeutic device comprises a reservoir with oxygen, particularly preferably medical oxygen, or is connected to such a reservoir, in order to supply oxygen from the reservoir into the respiratory system of the patient. It may be achieved by this embodiment of the invention that the supply of oxygen to the patient during resuscitation is improved, in particular for improved artificial respiration during minimal passive respiratory movements taking place during cardiac compression. Preferably, the oxygen supply is triggered by the monitoring device. A specific amount of medical oxygen is insufflated endotracheally from the oxygen reservoir, particularly preferably between 4 and 16 liters per minute, particularly preferably between 6 and 10 liters per minute.

A preferred respiratory therapeutic device also uses a pump for artificial respiration with oxygen or an oxygen-containing mixture, preferably an oxygen-air mixture, by means of which an artificial respiration volume, preferably individually predetermined, may be insufflated at a predetermined pressure and at a predetermined frequency in the cardiac compression resting phases for pulmonary resuscitation.

A preferred respiratory therapeutic device comprises a tube which may be positioned endotracheally, which is preferably guided through the puncture cannula. In this embodiment of the invention, the oxygen or the oxygen-containing mixture may be preferably controlled by means of a pump or by adjusting the pressure of the oxygen reservoir, supplied in the form of individual artificial respiration movements through the tube.

In a preferred embodiment of the invention, it is provided that as soon as the detection device determines respiratory arrest, after a certain latency period the trachea is perforated by means of the puncture unit below the larynx and an artificial respiration tube is pushed endotracheally through the cannula lumen towards the lungs. The artificial respiration tube has preferably only a slightly smaller diameter than the cannula. It is pushed towards the lungs, preferably between 5 and 15 centimetres, particularly preferably approximately 10 centimetres. Preferably in the upper third of the tube a cuff is provided. By filling the cuff with oxygen the trachea wall is sealed. As a result, advantageously the aspiration of foreign bodies, for example vomit, may be avoided.

Preferably, the respiratory therapeutic device comprises at least one reservoir with at least one drug or is connected to such a reservoir in order to supply the drug from the reservoir into the respiratory system of the patient. Particularly preferably, the respiratory therapeutic device may supply a plurality of drugs and to this end comprises one or more drug reservoirs and/or is connected thereto, such as for example in U.S. Pat. No. 5,405,362, the entire relevant contents thereof incorporated into the present disclosure by reference. The supply of the drug(s) is preferably triggered by the monitoring device. The drug(s) is (are) preferably in solution.

In a preferred embodiment, the respiratory therapeutic device has a thin catheter which particularly preferably is able to be pushed automatically through the lumen of the endotracheally located tube or through the lumen of the puncture cannula into the wind pipe. The catheter may, for example, be used to supply the drug (s) or by activating a vacuum be used to suck up aspirated material. Preferably, the catheter is pushed towards the lungs approximately 10 to 30, particularly preferably approximately 20 centimetres into the wind pipe. The active substance, adrenalin, is considered as a drug, for example. With this embodiment of the invention, it is advantageously achievable to deliver the drug via the catheter deep into the trachea and/or to suck up aspirated material, in order to optimise the mechanical attempts at resuscitation. The suctioned material is preferably collected in a sealed container.

The item of clothing is, or preferably comprises, a harness, belt, a jacket or a shirt. The harness may, for example, be a shoulder harness or a shoulder or underarm holster. The jacket may, for example, be configured in a similar manner to the commercially available LifeShirt. Moreover, components of the invention (for example energy sources) or parts thereof may be accommodated in other items of clothing (for example the soles of shoes) or aids which are carried (for example a walking stick).

The monitoring device is preferably provided with means for determining a cardiac and/or respiratory arrest, particularly preferably at least one means from the group of means which comprises: ECG unit, ultrasound unit, stethoscope, infrared unit, expansion sensor. The ECG unit comprises at least two electrodes in order to receive an electrocardiogram. The ultrasound unit may preferably receive a sonogram. With the stethoscope, for example, the heart sounds and/or lung activity may be monitored. The preferred stethoscope is an electronic stethoscope, which is able to convert the heart sound into an electrical signal, preferably by means of a microphone. Movements of the rib cage related to the respiration may be detected by means of the expansion sensor.

Preferably, the device according to the invention comprises a memory device in order to store data provided by other devices, in particular the monitoring device. The memory device preferably stores data which is provided from one or more means for determining a cardiac or respiratory arrest, for example the ECG unit, the ultrasound unit, the stethoscope, the infrared unit or the expansion sensor. A preferred memory device comprises sufficient memory capacity in order to store signals for a time period of up to 24 hours. The memory device is preferably arranged on the item of clothing.

In a preferred embodiment of the invention, the device for the medical care of a patient in an emergency comprises a positioning device in order to detect the current position coordinates of the wearer. The positioning device may, for example, comprise a means which may be located by a direction-finding transmitter and/or receiver. It may also comprise a device for determining the position by using a satellite-assisted positioning system, for example the GPS positioning system or the future Galileo system. Advantageously, the positioning device comprises a means for positioning by means of a mobile radio network, for example a GSM (Global System for Mobile Communications) network. This type of positioning utilizes the fact that each mobile radio transmitter and/or receiver is registered for the use of the mobile radio service in a cell, of which the range is known. Although this type of positioning possibly does not have the accuracy of satellite-assisted positioning, for example when, due to a lower number of transmitter masts in an area, one radio cell encompasses a large area, the mobile radio positioning system may be of use as an additional possibility for positioning, when the more accurate satellite-assisted positioning is not able to be implemented, for example in enclosed spaces or tunnels.

Advantageously, the positioning device comprises means for associating detected position coordinates with generally understandable local information, for example place, road, house number and floor level. A preferred positioning device comprises means to identify a rescue service point which is geographically the closest to the wearer. The positioning device is preferably arranged on the item of clothing.

Preferably the device according to the invention comprises a communication device for transmitting a message to a remote receiver, for example a rescue service point. The communication device is preferably forwarded to an alarm device in order to send an alarm to the receiver automatically and preferably by telephone, for example by a mobile radio network. The communication device is to this end expediently provided with a mobile radio transmitter and/or receiver, which for example uses GSM services or UMTS services. The mobile radio transmitter and/or receiver may, at the same time, be the means for GSM positioning or form a unit therewith. The system according to the invention is, however, not limited to current conventional mobile radio services (GSM and UMTS); but a transmitter and/or receiver for any type of wide-ranging wireless communication is conceivable.

Preferably, the communication device may communicate to the receiver information about the condition of the patient. The message transmitted to the external receiver may transmit information about cardiac malfunction of the patient and/or electrocardiographic signals thereof, preferably the electrocardiographic signals over a time period, which includes at least three, and at most 60, minutes. As a result of this embodiment of the invention it may be achieved that the receiver has been previously informed about the type of cardiac malfunction, so that it may take appropriate measures more rapidly. Preferably, the communication device communicates to the receiver about the identity of the patient, particularly preferably in accordance with data protection laws. The message to the receiver may, for example, contain a patient identification number.

Preferably, the communication device communicates to the receiver about the location of the patient, preferably by means of automatic speech synthesis. To this end, the communication device is preferably operatively connected to the positioning device. Expediently, the message transmitted to the receiver includes the result of satellite-assisted positioning, the result of the positioning by means of a mobile radio network and/or other location information, in order to allow thereby a rapid and as accurate as possible communication to the external receiver about the location of the patient. Expediently, the message sent to the receiver comprises information about whether the transmission of the message has been triggered manually or automatically. The communication device preferably has a self-test function, which regularly, for example once a day, creates a test connection to the external receiver and particularly preferably displays this process via a visual display as successful or failed. This test function may preferably also at any time be carried out manually by the wearer by pressing on a button.

In a further preferred embodiment of the present invention, the communication device comprises a means for manual activation by which the transmission of a message to the external receiver, preferably a rescue service, is triggered. By the means for manual activation, the possibility is provided to the patient to transmit a message to the external receiver when the patient is, for example, in an emergency situation, which is not recognised by the system according to the invention and/or may not be recognised, for example an emergency situation, which has not been triggered by cardiac malfunction, or even when the patient has doubts about whether the system according to the invention is operating correctly.

Preferably, the communication device is developed to form a device for producing a speech connection between the patient and/or the surroundings thereof and the external receiver, preferably the rescue service, or a further external receiver. An achievable advantage of this embodiment of the invention is that a consultation between the patient and the rescue service point is possible, for example in order to eliminate false alarms or in order to speak to a third party, for example a first aider, passer-by or relative where the patient is located, for example to specify the location of the attack, to communicate the sequence of events or to communicate information, as to whether immediate measures are necessary. To this end, the communication device is expediently provided with a handsfree means. In one embodiment of the invention, the handsfree means are developed such that passers-by may be made aware of the condition of the wearer. The communication device is preferably arranged on the item of clothing.

The device according to the invention preferably comprises at least one interface device for transmitting data provided from other equipment of the device to an external medium, particularly preferably the monitoring device. Expediently, an interface device is an interface according to the USB (Universal Serial Bus) standard and/or according to the Bluetooth Standard. The interface device is preferably arranged on the item of clothing.

In a preferred embodiment, the device according to the invention has a visual and/or acoustic and/or vibrating display device for displaying status information, warnings and/or system information. For example, status information about the energy supply, system information relative to a correct positioning of the electrodes and/or relative to a correct connection of the electrodes to the central control unit and possibly warnings when obvious cardiographic or respiratory-specific signals occur or the imminent expiry date of the drugs or the oxygen may be displayed. By means of the visual and/or acoustic and/or vibrating display device the patient may expediently be informed, for example, about possibly occurring errors and, in particular, about irregularities determined by the monitoring device, which could be attributed to cardiac and/or respiratory malfunctions. The display device is preferably arranged on the item of clothing.

The device according to the invention preferably comprises an energy device for supplying other equipment of the device with energy. The energy device may, for example, comprise a rechargable battery or a fuel cell. The energy device is preferably arranged on the item of clothing. Electrical conductors to the other devices are preferably also arranged on the item of clothing.

In a preferred embodiment of the device according to the invention, one or more devices or parts from one or more devices from the group of devices which includes: the monitoring device, energy device, memory device, positioning device, direction-finding device, communication device, interface device, display device, energy device are accommodated in a central control unit. The control unit does not necessarily have to be arranged on the item of clothing or to be worn directly against the body. For example, it is conceivable that the control unit is configured such that a patient, when for example lying in bed, is able to position the control unit in the vicinity thereof. As a result of this embodiment of the invention, a visit from paramedic units may also be facilitated for the patient in that the patient does not have to carry the control unit. In a further preferred embodiment, the control unit is releasably fastened, for example on a belt, via which the control unit may be fixedly attached, so that the weight of the central control unit hinders and/or weighs down the patient as little as possible.

The equipment of the device according to the invention and the components thereof may be in communicative connection with one another in a wired or wireless manner. Expediently, the wireless connection is a blue tooth connection, a different radio frequency connection or an infrared connection. However, other wireless connections are also conceivable, such as for example a newly developed standard for radio connections with short ranges. Preferably, devices or components, for example electrodes attached to the body of the patient, communicate in an acoustic or visual or vibrating manner, when the range of the wireless connection to a different device or component to which it is connected, is exceeded.

In a preferred embodiment, the device according to the invention comprises a programmable device, preferably at least one microprocessor, in order to control the therapeutic devices based on the psychological parameters detected by the monitoring device. The programmable device is preferably accommodated in the monitoring device. A control program is preferably operated on the device, for example mutatis mutandis, according to that disclosed in U.S. Pat. No. 5,156,148. The relevant contents of the aforementioned document are incorporated into the present disclosure by reference.

BRIEF DESCRIPTION OF THE DRAWINGS

The invention is described in more detail hereinafter with reference to schematic drawings and embodiments with further details, in which.

DESCRIPTION WITH REFERENCE TO EMBODIMENTS

Figure 1:
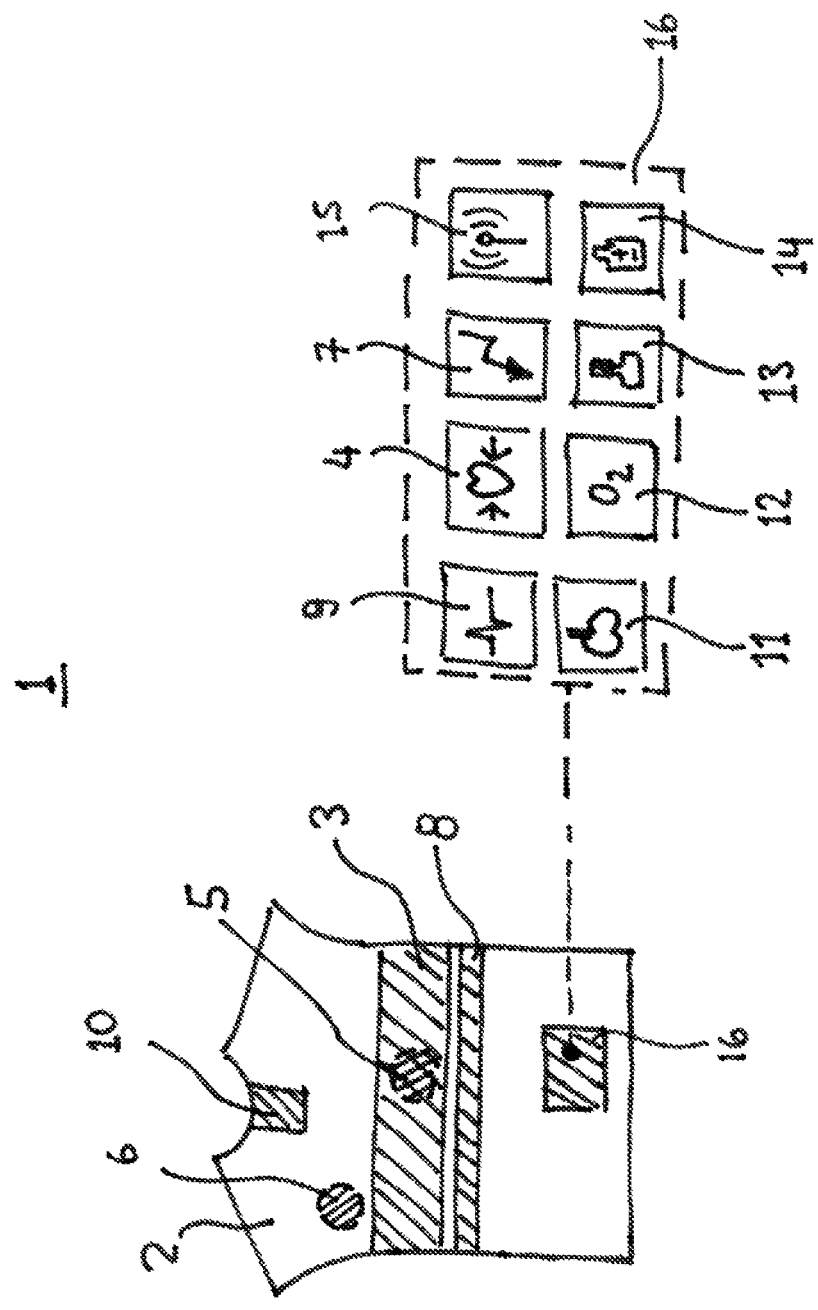
FIG. 1 shows a schematic block diagram of a device according to the invention for the medical care of a patient in an emergency.
Figure 2:
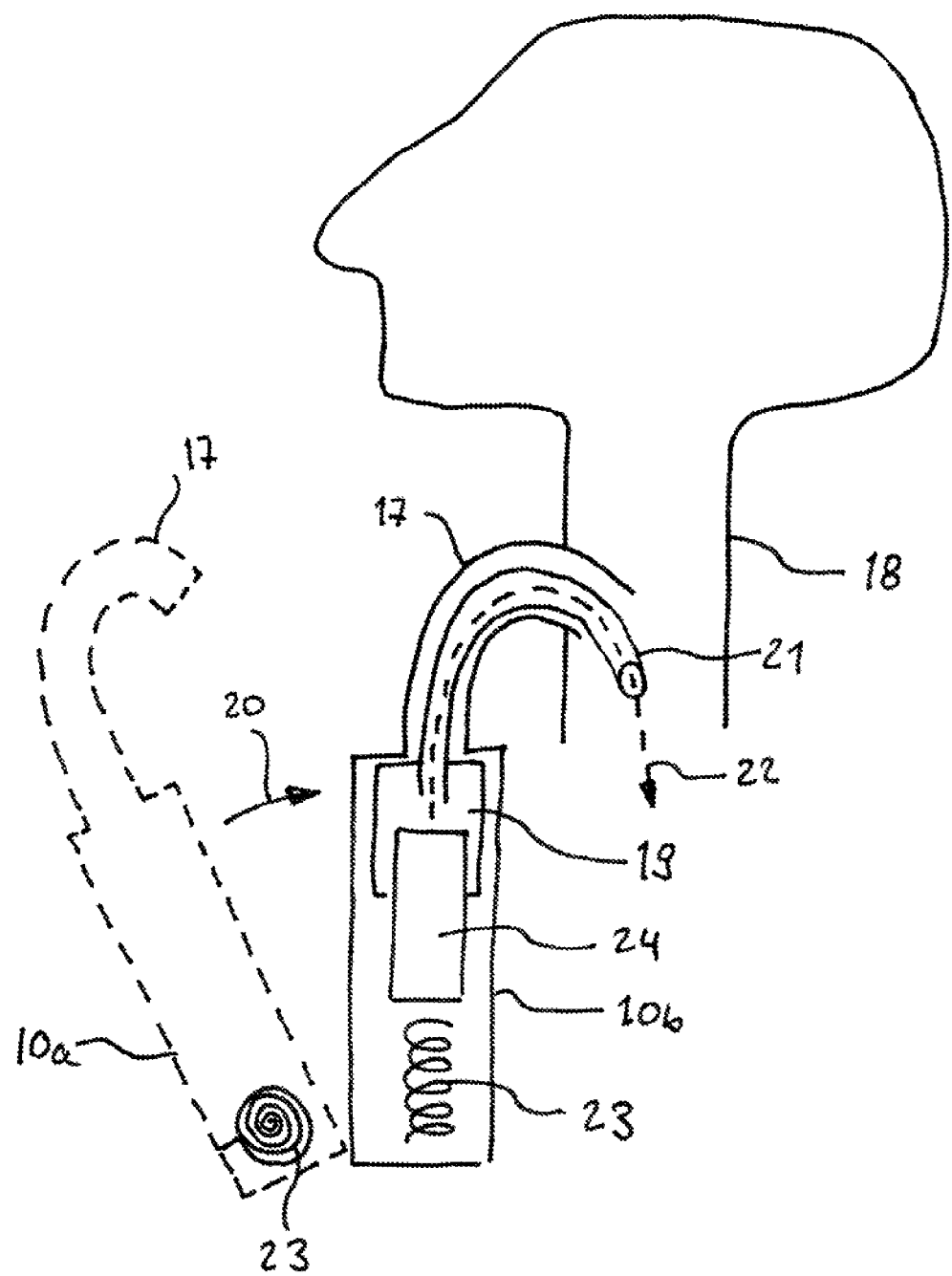
FIG. 2 shows a schematic view of a puncture unit for the trachea.

A device for the medical care of a patient in an emergency according to the present invention is shown schematically in FIG. 1. The device 1 comprises a shirt 2 which tightly fits against the body of its wearer. On the shirt 2 in the region of the transition from the central to the lower third of the breast bone of the wearer a tubular airbag 3 of a cardiac compression device 4 is sewn into the shirt 2, in order to carry out in an emergency a cardiac compression according to the thorax pump method for maintaining a minimum circulation. The airbag 3 may be inflated and emptied by means of a pump, such as for example disclosed in EP 1 550 398 A1. In a further embodiment of the invention, via a pneumatic plunger or spring mechanism with a bearing surface of approximately 5×10 cm along the breast bone, the breast bone is pressed in the transition region from the central to the lower third at a frequency of approximately 100 per minute by approximately 6 cm against the spinal column. The dwell time in the maximum compressed position is thus the same as that of the relaxed position, so that the compression and relaxed phases are of the same duration. In order to allow the pressure against the spinal column, the harness and/or the shirt have to adopt a rigid state in the back region for the respective duration of the cardiac compression, for example by means of airbags arranged at that point. Moreover, via this unit, access may be created to the bone marrow of the breast bone via a puncture cannula for the administration of injectable or infusible drugs.

Moreover, two electrodes 5, 6 of a defibrillator 7 are sewn into the shirt 2 which, if required, release gel or allow protection of the skin in another manner and may then carry out a cardioversion. Moreover, an expansion sensor 8 of a monitoring device 9 is fitted into the shirt in order to monitor the respiratory activity of the wearer.

In the upper part of the shirt 2 is arranged the puncture device 10a, 10b of a respiratory therapeutic device 11 which may perforate the trachea 18 of the patient with a semi-circular puncture cannula 17 of approximately 14 mm diameter, as a puncture unit. To this end, pneumatic means or a pretensioned spring are provided, similar to the autoinjector disclosed in U.S. Pat. No. 5,405,362. An oxygen unit 12 of the respiratory therapeutic unit uses a sealed reservoir 19 in which medical oxygen is stored. The reservoir is accommodated in the puncture device 10a, 10b or in an oxygen unit 12 of the central control unit. As soon as the monitoring device 9 detects a respiratory arrest, after a certain latency time, the trachea of the wearer is perforated below the larynx by means of the semi-circular puncture cannula 17, by the puncture device being moved pneumatically or by spring force in the direction of the arrow 20 from the position 10a into the position 10b. Subsequently, an artificial respiration tube 21 which has only a slightly smaller diameter than the puncture cannula, is pushed by a spring 23 and a plunger 24 through the cannula lumen approximately 10 cm endotracheally towards the lungs. After the tube has been completely pushed forward, a cuff is filled with oxygen in order to seal the tube 21 from the trachea wall, and thus to avoid the aspiration, for example, of vomit. From the oxygen reservoir 19, as indicated by the arrow 22, approximately 8 liters per minute of medical oxygen are insufflated, in order to supply with oxygen minimal passive respiratory movements taking place during the cardiac compression. In the compression resting phases, the oxygen and/or oxygen-containing gas mixture is insufflated by means of a pump, not shown, at a predetermined frequency in the form of individual artificial respiration movements.

A medical device 13 uses a sealed reservoir in which different emergency drugs (for example adrenalin) are present, separated from one another and in solution. Via a thin catheter, which in an emergency is automatically pushed through the lumen of the endotracheally located tube 21, approximately 20 cm into the wind pipe, the drugs may be automatically administered deep into the trachea in order to optimise the mechanical resuscitation attempts. Aspirated material may also be suctioned via the catheter by means of a pump as a vacuum source and collected in a sealed container.

Oxygen and drug reservoirs, pumps and control and evaluation devices as well as an energy device 14, a GSM transmitter and receiver, a direction-finding device and a GPS positioning device 15 are combined in a central control unit 16, which is also sewn into the shirt 2. By means of conductors and tubes sewn into the shirt 2, the central control unit 16 is connected to the other aforementioned components of the device.

The features disclosed in the aforementioned description, the claims and the drawings may be of importance both individually and also in any combination for the development of the invention in its different embodiments.

The invention claimed is:

1. A device for the medical care of a patient in an emergency comprising:
   an item of clothing, wherein the item of clothing is worn by the patient on the body;
   a monitoring device arranged on the item of clothing, wherein the monitoring device monitors at least one physiological function of the patient to determine an emergency; and
   a therapeutic device for treating the patient when the monitoring device determines an emergency, wherein the therapeutic device is:
      arranged on the item of clothing, and
      operatively connected to the monitoring device, wherein the monitoring device can, without the active involvement of the patient or a third party, trigger the therapeutic device when the monitoring device determines an emergency, and
      wherein the therapeutic device is a respiratory therapeutic device that endotracheally supplies oxygen, an oxygen-containing gas mixture and/or at least one drug, wherein the respiratory therapeutic device comprises a puncture unit for perforating the trachea of the patient below the larynx.

2. The device according to claim 1, wherein the device comprises a second therapeutic device.

3. The device according to claim 2, wherein the second therapeutic device is a defibrillator.

4. The device according to claim 2, wherein the second therapeutic device is a cardiac compression device for cardiac resuscitation.

5. The device according to claim 1, wherein the respiratory therapeutic device
   comprises a reservoir, or
   is operatively connected to a reservoir, and
wherein:
   the reservoir is an oxygen or oxygen-containing gas reservoir, and
   the respiratory therapeutic device supplies oxygen or the oxygen-containing gas mixture from the reservoir into the respiratory system of the patient.

6. The device according to claim 1, wherein the respiratory therapeutic device comprises means for supplying at a predetermined frequency oxygen or an oxygen-containing gas mixture endotracheally.

7. The device according to claim 1, wherein the respiratory therapeutic device
   comprises a reservoir, or
   is connected to a reservoir
wherein the reservoir contains said at least one drug supplied by the respiratory therapeutic device and wherein the drug from the reservoir is supplied to the respiratory system of the patient.

8. The device according to claim 1, wherein the respiratory therapeutic device comprises a catheter, wherein the catheter is arranged so that it can be pushed into the trachea.

9. The device according to claim 8, wherein the respiratory therapeutic device comprises means for:
   supplying a drug via the catheter, or
   suctioning material out of the trachea and/or the bronchial tubes.

10. The device according to claim 1, wherein the item of clothing comprises a harness, a jacket or a shirt.

11. The device according to claim 1, wherein the monitoring device comprises means for determining a cardiac or respiratory arrest.

12. The device according to claim 11, wherein the monitoring device comprises a device selected from the group consisting of ECG unit, ultrasound unit, stethoscope, infrared unit, and expansion sensor, and wherein the monitoring device detects a cardiac or respiratory arrest.

13. The device according to claim 1, wherein the device comprises a memory device for storing data provided by the monitoring device or the therapeutic device.

14. The device according to claim 1, wherein the device comprises a positioning device for detecting current position coordinates of the patient wearing the item of clothing.

15. The device according to claim 1, wherein the device comprises a communication device for transmitting a message to a remote receiver.

16. The device according to claim 1, wherein the device comprises an interface device for transmitting data provided by the monitoring device or the therapeutic device to an external medium.

17. The device according to claim 1, wherein the device comprises a visual and/or acoustic display device for displaying status information, warnings and/or system information.

18. The device according to claim 1, wherein the device comprises an energy device for supplying energy to the monitoring device or the therapeutic device.

19. The device according to claim 1, wherein the monitoring device or the therapeutic device is accommodated in a central control unit.

20. The device according to claim 13, wherein the memory device is accommodated in a central control unit.

21. The device according to claim 14, wherein the positioning device is accommodated in a central control unit.

22. The device according to claim 15, wherein the communication device is accommodated in a central control unit.

23. The device according to claim 16, wherein the interface device is accommodated in a central control unit.

24. The device according to claim 17, wherein the display device is accommodated in a central control unit.

25. The device according to claim 18, wherein the energy device is accommodated in a central control unit.

* * * * *